United States Patent
Robinson, II

(10) Patent No.: US 12,161,735 B2
(45) Date of Patent: Dec. 10, 2024

(54) FLEXIBLE COLOR SUBSTRATE

(71) Applicant: L'Oreal, Paris (FR)

(72) Inventor: Michael P. Robinson, II, Brooklyn, NY (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 17/816,207

(22) Filed: Jul. 29, 2022

(65) Prior Publication Data

US 2024/0033190 A1 Feb. 1, 2024

(51) Int. Cl.
*A61K 8/02* (2006.01)
*A45D 37/00* (2006.01)
*A61K 8/06* (2006.01)
*A61Q 1/02* (2006.01)

(52) U.S. Cl.
CPC .............. *A61K 8/0208* (2013.01); *A61K 8/06* (2013.01); *A61K 2800/10* (2013.01); *A61K 2800/43* (2013.01); *A61K 2800/87* (2013.01); *A61Q 1/025* (2013.01)

(58) Field of Classification Search
CPC .............. A61K 8/0208; A61K 2800/10; A61K 2800/43; A61K 2800/87; A61Q 1/025; A45D 37/00
See application file for complete search history.

(56) References Cited

U.S. PATENT DOCUMENTS

| | | | |
|---|---|---|---|
| 6,190,730 B1 | 2/2001 | Matsos et al. | |
| 9,215,920 B2 | 12/2015 | Dobler et al. | |
| 10,820,680 B1 * | 11/2020 | Macri | A45D 40/30 |
| 2010/0239619 A1 | 9/2010 | Hurwitz | |
| 2012/0055498 A1 | 3/2012 | Haddad | |
| 2015/0044410 A1 | 2/2015 | Kim et al. | |
| 2016/0324299 A1 | 11/2016 | Samain et al. | |

FOREIGN PATENT DOCUMENTS

| | | | |
|---|---|---|---|
| EP | 1266589 A2 | 12/2002 | |
| EP | 2008544 A1 | 12/2008 | |
| FR | 2886146 A1 | 12/2006 | |
| FR | 2886146 | * 8/2007 | |
| FR | 3015871 B1 | 2/2016 | |
| JP | 2009195318 A | 9/2009 | |
| KR | 20110117437 A | 10/2011 | |
| KR | 101378789 B1 | 3/2014 | |
| KR | 101708239 B1 | 2/2017 | |
| WO | 2005027684 A1 | 3/2015 | |
| WO | 2021085203 A1 | 5/2021 | |

* cited by examiner

*Primary Examiner* — Mina Haghighatian

(74) *Attorney, Agent, or Firm* — CHRISTENSEN O'CONNOR JOHNSON KINDNESS PLLC

(57) ABSTRACT

A flexible substrate including a transparent release, a protective layer disposed on top of the transparent release, a color layer disposed on top of the protective layer, and a carrier layer disposed on top of the color layer, wherein the carrier layer is removably coupled to the flexible substrate and wherein the carrier layer prevents the color layer from transferring, where when the carrier layer is removed and the flexible substrate is applied to a surface, pressure applied to the transparent release results in transferring the protective layer and the color layer to the surface.

20 Claims, 12 Drawing Sheets

FLEXIBLE COLOR SUBSTRATE

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a flexible substrate including a transparent release, a protective layer disposed on top of the transparent release, a color layer disposed on top of the protective layer, and a carrier layer disposed on top of the color layer, wherein the carrier layer is removably coupled to the flexible substrate and wherein the carrier layer prevents the color layer from transferring, wherein, when the carrier layer is removed and the flexible substrate is applied to a surface, pressure applied to the transparent release results in transferring the protective layer and the color layer to the surface is disclosed.

In another aspect, a system including a flexible substrate including a transparent release, a protective layer disposed on top of the transparent release, a color layer disposed on top of the protective layer, and a carrier layer disposed on top of the color layer, wherein the carrier layer is removably coupled to the color layer and wherein the carrier layer prevents the color layer from transferring, where, when the carrier layer is removed and the flexible substrate is applied to a surface, pressure applied to the transparent release results in transferring the protective layer and the color layer to one or more primed areas of the surface, and a primer, wherein the primer is configured to be applied to the surface to create the one or more primed areas of the surface is disclosed.

In yet another aspect, a method of applying a cosmetic with the flexible substrate of claim 1, the method comprising removing the carrier layer from the flexible substrate of claim 1, applying the flexible substrate to a surface, applying pressure to the flexible substrate in one or more places corresponding with one or more desired locations of the surface, transferring the color layer and the protective layer to the surface, and removing the transparent release from the surface is disclosed.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
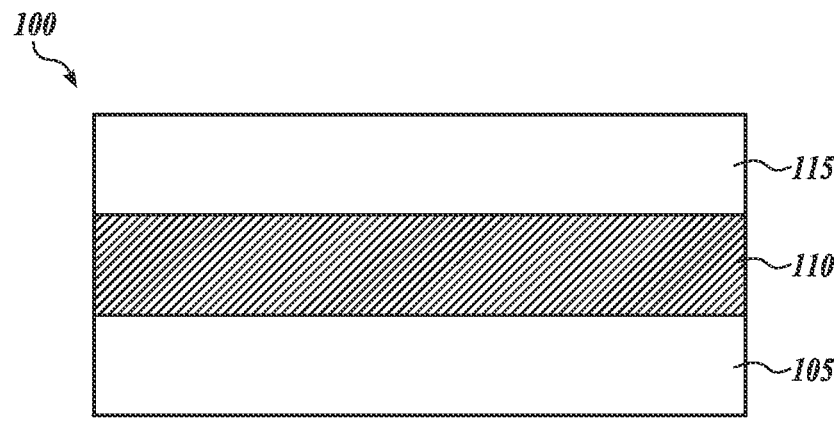
FIG. 1A is an example flexible substrate, in accordance with the present technology.

While illustrative embodiments have been illustrated and described, it will be appreciated that various changes can be made therein without departing from the spirit and scope of the invention.

Described herein is a flexible substrate including a color layer and a protective layer configured to be transferred onto a surface. In some embodiments, the surface is skin, hair, or nails. In some embodiments, the flexible substrate further includes a carrier layer configured to protect the color layer and the protective layer that can be peeled off before application to a surface.

In one aspect, a flexible substrate including a transparent release, a protective layer disposed on top of the transparent release, a color layer disposed on top of the protective layer, and a carrier layer disposed on top of the color layer, wherein the carrier layer is removably coupled to the flexible substrate and wherein the carrier layer prevents the color layer from transferring, where, when the carrier layer is removed and the flexible substrate is applied to a surface, pressure applied to the transparent release results in transferring the protective layer and the color layer to the surface is disclosed.

In some embodiments, the flexible substrate further includes a pattern layer, where when pressure is applied to the transparent release, the pattern layer transfers to the surface. In some embodiments, the flexible substrate further includes a stencil layer including one or more openings, where when pressure is applied to the transparent release, color is transferred through the one or more openings in the stencil layer, and the stencil layer is not transferred to the surface.

In some embodiments, the flexible substrate further includes one or more additive layers, where when pressure is applied to the transparent release, the additive layer transfers to the surface. In some embodiments, the one or more additive layers are selected from: a UV protection layer, a moisturizing layer, a fragrance layer, a cooling layer, and a heating layer.

In some embodiments, the surface is skin. In some embodiments, the flexible substrate further includes an adhesive layer configured to adhere the color layer and the protective layer to the surface, where the adhesive layer is disposed on top of the color layer. In some embodiments, the flexible substrate further includes a finish layer, where the finish layer is configured to provide a particular finish to the surface when transferred.

In another aspect, a system including a flexible substrate including a transparent release, a protective layer disposed on top of the transparent release, a color layer disposed on top of the protective layer, and a carrier layer disposed on top of the color layer, wherein the carrier layer is removably coupled to the color layer and wherein the carrier layer prevents the color layer from transferring where, when the carrier layer is removed and the flexible substrate is applied to a surface, pressure applied to the transparent release results in transferring the protective layer and the color layer to one or more primed areas of the surface, and a primer, wherein the primer is configured to be applied to the surface to create the one or more primed areas of the surface is disclosed.

In some embodiments, the primer is a high-solid emulsion adhesive.

In some embodiments, the flexible substrate further includes a pattern layer disposed underneath the color layer, where when pressure is applied to the transparent release, the pattern layer transfers to the one or more primed areas of the surface. In some embodiments, the flexible substrate further comprises a stencil layer comprising one or more openings, wherein the stencil layer is on top of the color layer, and where when pressure is applied to the transparent release, color is transferred through the one or more openings in the stencil layer, and the stencil layer is not transferred to the one or more primed areas of the surface. In some embodiments, flexible substrate further includes one or more additive layers, wherein when pressure is applied to the transparent release, the pattern layer transfers to the one or more primed areas of the surface. In some embodiments, the one or more additive layers are selected from a UV protection layer, a moisturizing layer, a fragrance layer, a cooling layer, and a heating layer.

In yet another aspect, a method of applying a cosmetic with the flexible substrate of claim 1, the method including removing the carrier layer from the flexible substrate as described herein, applying the flexible substrate to a surface, applying pressure to the flexible substrate in one or more places corresponding with one or more desired locations of the surface, transferring the color layer and the protective layer to the surface, and removing the transparent release from the surface is disclosed.

In some embodiments, the method further includes applying a primer to the one or more desired locations of the surface before applying the flexible substrate, where the primer is configured to adhere to the color layer and the protective layer.

In some embodiments, the method further includes applying the flexible substrate to the surface, wherein the flexible substrate further comprises a stencil layer comprising a plurality of openings, applying pressure to the flexible substrate in one or more places corresponding with one or more desired locations of the surface, transferring the color layer and the protective layer through the one or more openings and removing the stencil layer from the surface. In some embodiments, the method further including applying a stencil layer to the surface before applying the flexible substrate to the surface, wherein the stencil layer comprises a plurality of openings, applying pressure to the flexible substrate in one or more places corresponding with one or more desired locations of the surface, transferring the color layer and the protective layer through the one or more openings, and removing the stencil layer from the surface.

In some embodiments, the method further comprises transferring a pattern layer of the flexible substrate to the surface. In some embodiments, the method further comprises transferring one or more additive layers of the flexible substrate to the surface.

FIG. 1A is an example flexible substrate 100, in accordance with the present technology. In some embodiments, the flexible substrate 100 includes a transparent release 105, a color layer 110, and a carrier layer 115. While flexible substrate 100 is illustrated as a rectangle, flexible substrate 100 can take any shape. In some embodiments, the flexible substrate 100 is shaped or sized to fit onto a particular surface. In an example, the flexible substrate 100 may be shaped as a top and bottom lip.

In some embodiments, the transparent release 105 is configured to peel from the other layers (i.e., the color layer 110 and the carrier layer 115). In some embodiments, the transparent release 105 is plastic. In some embodiments, the transparent release 105 is selected from polyethylene (PE), polyurethane (PU), biaxially-oriented polypropylene (BOPP), polyethylene terephthalate (PET), or combinations thereof.

In some embodiments, a color layer 110 is disposed on top of the transparent release 105. In some embodiments, the color layer 110 is a cosmetic. In some embodiments, the color layer 110 is a lip color, such as a lipstick or a lip tint, an eyeshadow, a blush, or an eyeliner. In some embodiments, the color layer 110 is not the same size as the flexible substrate. In some embodiments, the color layer 110 does not cover the entirety of the flexible substrate. For example, the color layer 110 may be discontinuous, such as patterned, polka dotted, or striped. In some embodiments, the color layer 110 may include more than one color. In some embodiments, the color layer 110 may include a finish, such as glitter, shimmer, shine, or matte. In some embodiments, the color layer 110 may include one or more moisturizing ingredient, such as petrolatum, shea butter, lanolin, beeswax, zinc oxide, menthol, cocoa butter, sesame oil, or a combination thereof. In some embodiments, the color layer 110 may include a fragrance or a flavoring.

In some embodiments, the flexible substrate 100 includes a carrier layer 115. In some embodiments, the carrier layer 115 is disposed above the color layer 110. In some embodiments, the carrier layer 115 is configured to peel off the color layer 110 without transferring the color layer 110 to the carrier layer 115. In some embodiments, the carrier layer 115 is configured to prevent the color layer 110 from transferring. In some embodiments, the carrier layer is configured to keep the color layer 110 from drying out, particulates, contamination, etc. In some embodiments, the flexible substrate 100 includes more than one carrier layer 115, located between transferrable layers (such as color layer 110) to allow a user to transfer each transferrable layer separately. In some embodiments, the carrier layer 115 is a silicon release. In some embodiments, the carrier layer 115 is made of a non-woven specialty material. In some embodiments, the carrier layer 115 is larger than the flexible substrate 100, so that part of the carrier layer 115 hangs off the flexible substrate 100. In some embodiments, the carrier layer 115 includes a tab to aid in removing the carrier layer 115 from the flexible substrate.

Figure 6A:
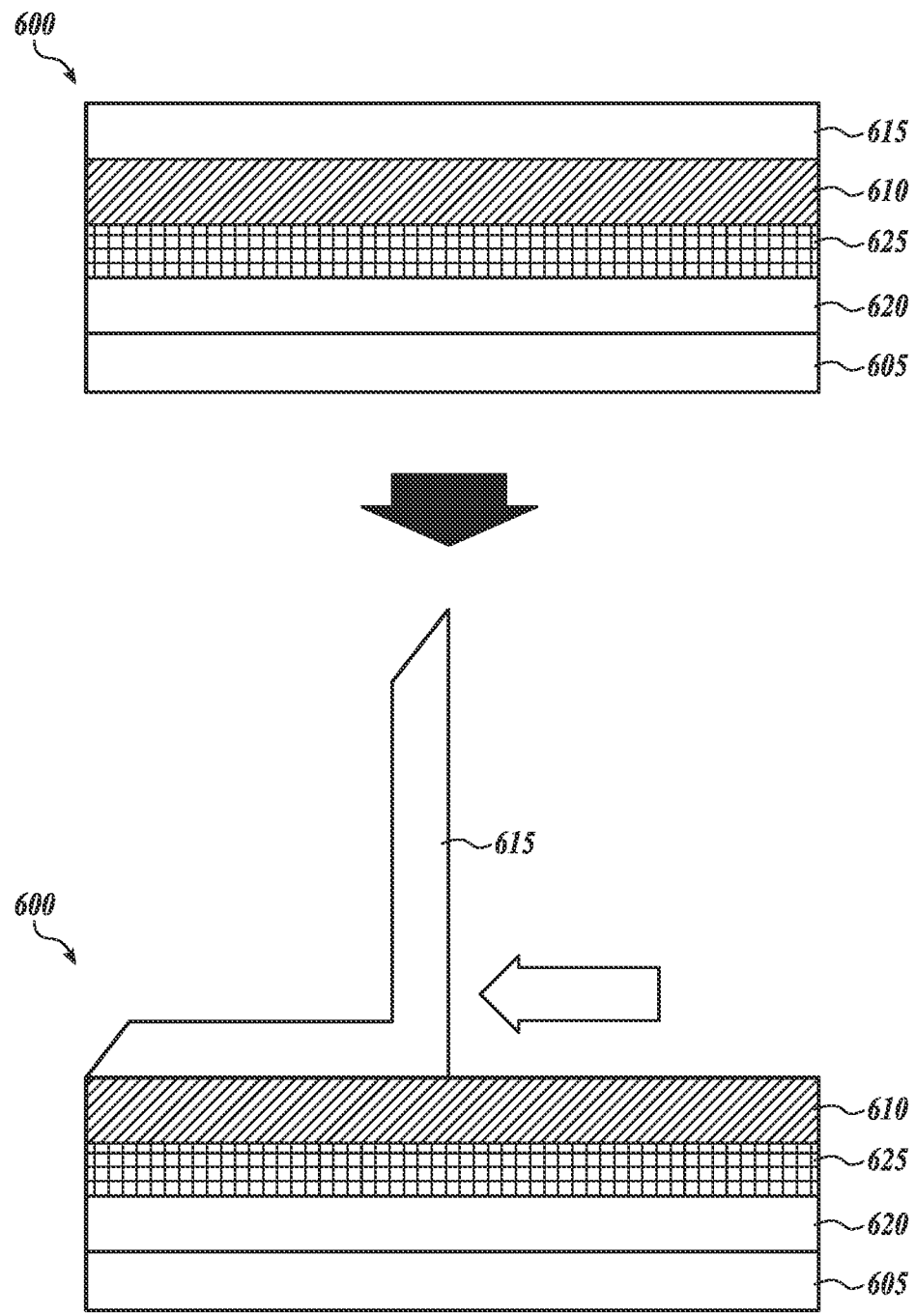
FIGS. 6A-6C illustrates an example method of using the flexible substrate of FIG. 2A, in accordance with the present technology.
Figure 6C:
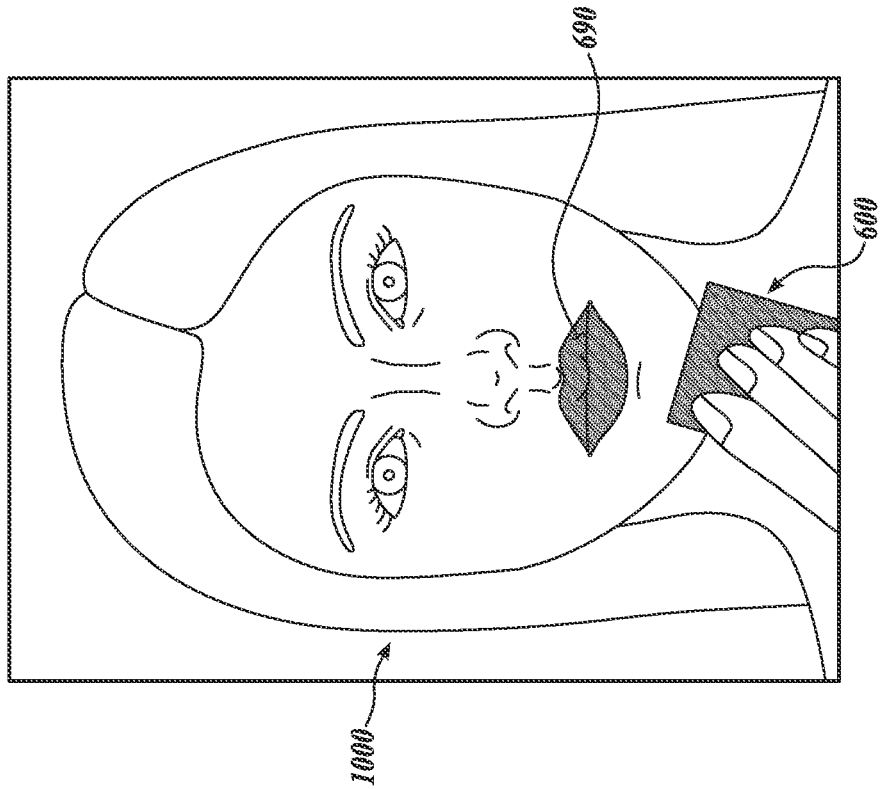
Figure 6B:
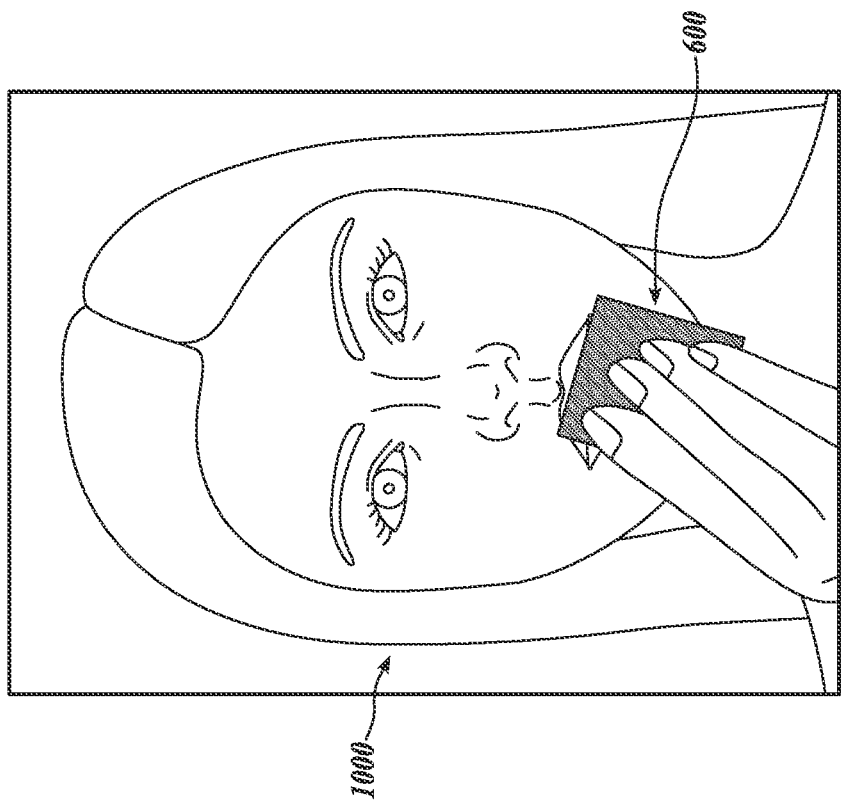

In operation, the carrier layer 115 is removed from the flexible substrate 100. In some embodiments, the carrier layer 115 is peeled off the flexible substrate 100. In some embodiments, the flexible substrate 100 is then placed on a surface, with the color layer 115 facing towards the surface, as illustrated in FIGS. 6A-6C. In some embodiments, pressure is applied to the transparent release 105. In some embodiments, the color layer transfers to the surface where pressure is applied. In some embodiments, after transferring the color layer, the transparent release is removed from the surface. In some embodiments, the surface is skin. In some embodiments, the surface is the lips, eyelids, cheeks, or nose.

Figure 1B:
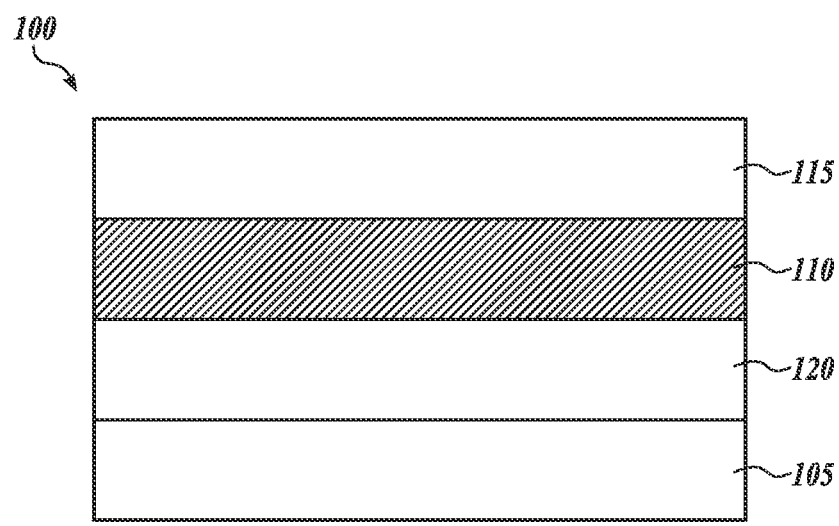
FIG. 1B is another example flexible substrate, in accordance with the present technology.

FIG. 1B is another example flexible substrate 100, in accordance with the present technology. In some embodiments, the flexible substrate 100 further includes a protective layer 120. In some embodiments, the protective layer 120 is a wax, such as beeswax, candelilla wax, polyolefin wax, or a combination thereof. In some embodiments, the protective layer 120 is configured to prevent the color layer 110 from smearing, smudging, or wiping away throughout the day. In some embodiments, the protective layer 120 prevents further transfer of the color layer 110 once applied to a surface. In some embodiments, the protective layer 120 is a powder, such as setting powder, translucent powder, talcum powder, or a combination thereof. In some embodiments, the protective layer is an oil such as mineral oil, castor oil, lanolin oil, silicon oil, vegetable oil, or a combination thereof.

In operation, when the flexible substrate 100 is applied to the surface, the color layer 110 and the protective layer 120 are transferred to the surface, simultaneously. In some embodiments, the flexible substrate 100 may include more than one carrier layer 115, so that the color layer 110 and the protective layer 120 may be applied sequentially. In some embodiments, when the protective layer 120 is transferred, it is transferred on top of the color layer 110. In this manner, the protective layer 120 prevents the color layer 110 from further transferring. The protective layer 120 may also prevent creasing, bleeding, smudging, or wiping off the color layer 110 from the surface, once transferred.

In some embodiments, before the flexible substrate 100 is applied to the surface, a primer is applied, as shown in FIGS. 7A-7D. In some embodiments, the primer is an adhesive. In some embodiments, the primer is a high-solid emulsion adhesive. In some embodiments, the color layer 110 is configured to adhere to the primer but not the surface. In this manner, when pressure is applied to the flexible substrate 100, the color layer 110 transfers only to the locations where primer has been applied.

Figure 2A:
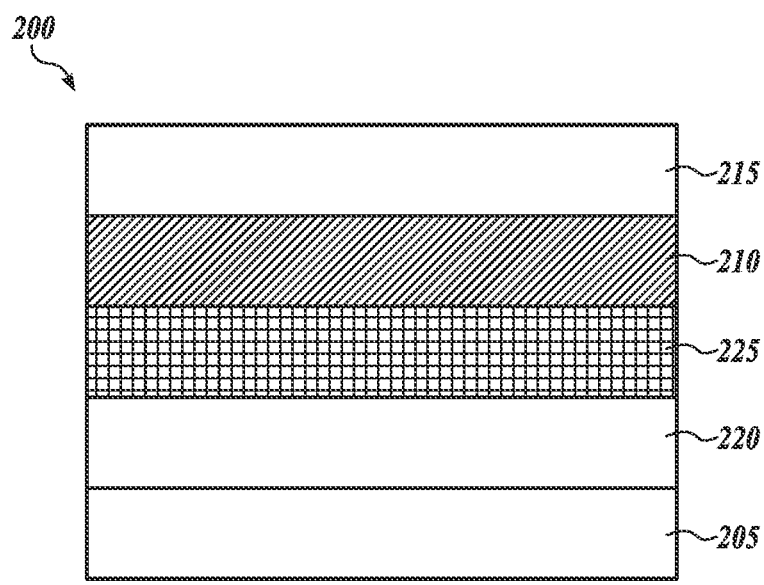
FIG. 2A is another example flexible substrate, in accordance with the present technology.

FIG. 2A is another example flexible substrate 200, in accordance with the present technology. In some embodiments, the flexible substrate includes a transparent release 205, a protective layer 220, a pattern layer 225, a color layer 210, and a carrier layer 215.

In some embodiments, the flexible substrate may further include a pattern layer 225. In some embodiments, the pattern layer 225 is a second color layer that is smaller or differently shaped from the color layer 110. In some embodiments, the pattern layer 225 is a printed pattern layer, which includes a binder and a pigment. In some embodiments, the pattern layer 225 is discontinuous, i.e., polka dots, stripes, houndstooth, etc. In some embodiments, the pattern layer 225 may be an image. In some embodiments, the pattern layer 225 may be made of a polymer, such as synthetic rubber, nylon, silicon, or a combination thereof. In some embodiments, the pattern layer 225 may be a tiled image or repeating pattern. In some embodiments, the pattern layer 225 may include glitter, shimmer, shine, or matte finish. In some embodiments, the pattern layer 225 is a single color, but in other embodiments, the pattern layer 225 is multicolored. In some embodiments, the pattern layer 225 is henna. In some embodiments, the pattern layer 225 includes a fragrance. In some embodiments, the pattern layer 225 includes a flavoring.

In operation, the pattern layer 225 is transferred onto the surface with the color layer 110. In some embodiments, the pattern layer 225 is transferred on top of the color layer 110, so that the color layer 110 is visible underneath the pattern layer 225. In some embodiments, the flexible substrate may include a plurality of pattern layers 225 configured to transfer on top of one another to create additional patterns. In some embodiments, the flexible substrate may include a plurality of pattern layers 225, each with a corresponding carrier layer 215, to prevent transfer between the plurality of pattern layers 225. In such embodiments, a user may select one or more pattern layers 225 to apply by removing the associated carrier layer 215 to expose the desired pattern layers 225.

Figure 2B:
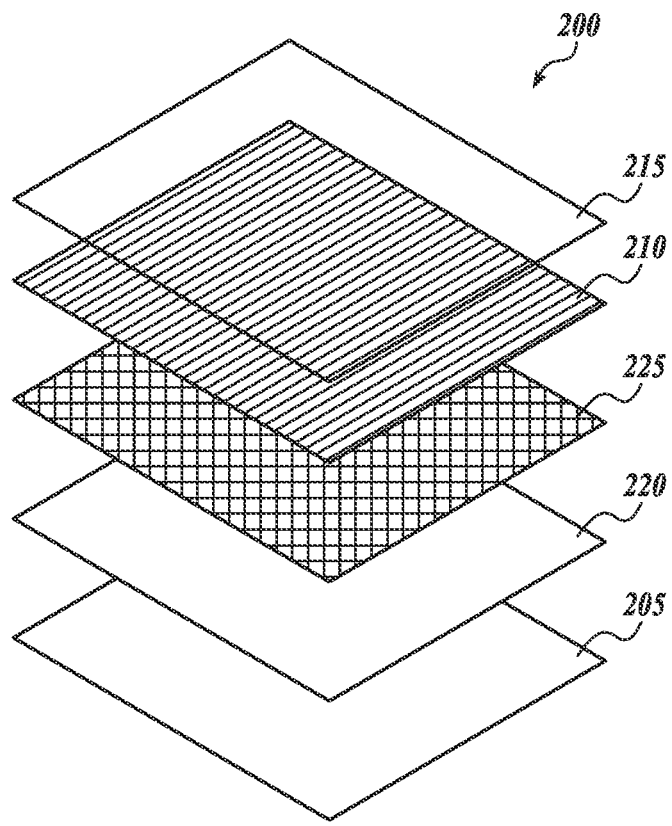
FIG. 2B is an expanded view of the flexible substrate of FIG. 2A, in accordance with the present technology.

FIG. 2B is an expanded view of the flexible substrate 200 of FIG. 2A, in accordance with the present technology. As described in FIG. 2A, in some embodiments, the flexible substrate includes a transparent release 205, a protective layer 220, a pattern layer 225, a color layer 210, and a carrier layer 215.

Figure 3A:
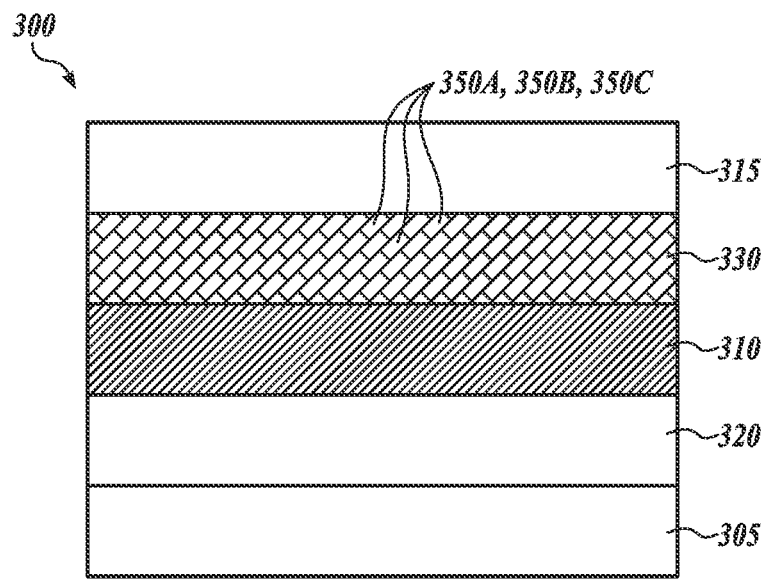
FIG. 3A is another example flexible substrate, in accordance with the present technology.

FIG. 3A is another example flexible substrate 300, in accordance with the present technology. In some embodiments, the flexible substrate 300 includes a transparent release 305, a protective layer 320, a color layer 310, a stencil layer 330, and a carrier layer 315. While the carrier layer 315 is illustrated as transparent, the carrier layer 315 may also be opaque.

In some embodiments, the flexible substrate 300 includes a stencil layer 330. In some embodiments, the stencil layer 330 includes a plurality of openings 350A, 350B, 350C. In some embodiments, the stencil layer 330 is made from the same material as the transparent release 305. In some embodiments, the stencil layer 330 is made from the same material as the carrier layer. In some embodiments, the plurality of openings 350A, 350B, 350C form a pattern or an image. In some embodiments, the flexible substrate 300 may have a plurality of stencil layers 330, so that plurality of stencil layers 330 are applied simultaneously. In some embodiments, the flexible substrate 300 may include multiple stencil layers 330 so that a user may select one or more stencil layers from the plurality of stencil layers 330 to apply. In this embodiment, the plurality of stencil layers may be attached to the removable substrate with an adhesive covering only an edge of the stencil, so that a user can flip through the plurality of stencils and select a desired stencil or stencils from the plurality of stencils. In some embodiments, the stencil layers 330 are removable, such as with a perforated edge. In some embodiments, the flexible substrate 300 is re-usable, and the user can select a different stencil layer for each application. In some embodiments, one or more stencil layers 330 may be removed and placed on the surface before applying the flexible substrate to the surface.

In operation, when the flexible substrate 300 is applied to a surface, and pressure is applied to the transparent release 305, the color layer 310 and the protective layer 320 transfer onto the surface through the plurality of openings on the stencil layer 330.

Figure 3B:
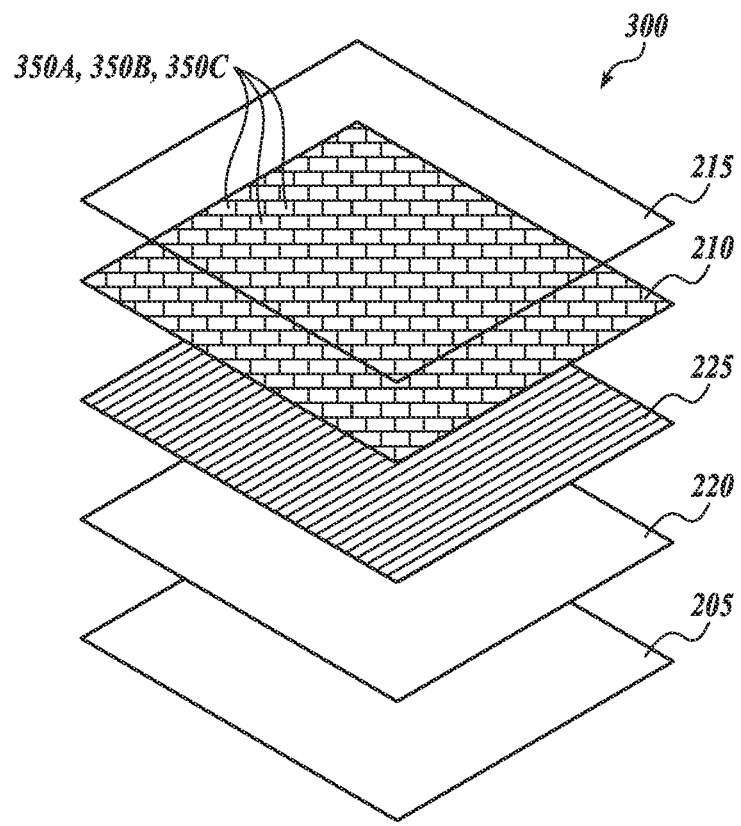
FIG. 3B is an expanded view of the flexible substrate of FIG. 3A, in accordance with the present technology.

FIG. 3B is an expanded view of the flexible substrate of FIG. 3A, in accordance with the present technology. As described in FIG. 3A, the flexible substrate 300 includes a transparent release 305, a protective layer 320, a color layer 310, a stencil layer 330, and a carrier layer 315. While the carrier layer 315 is illustrated as transparent, the carrier layer 315 may also be opaque.

Figure 4A:
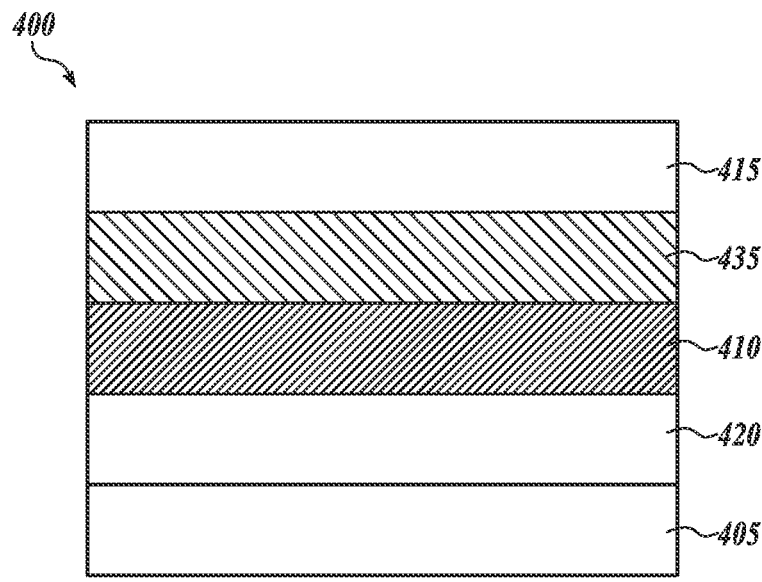
FIG. 4A is another example flexible substrate, in accordance with the present technology.

FIG. 4A is another example flexible substrate 400, in accordance with the present technology. In some embodiments, the flexible substrate includes a backing layer 405, a protective layer 420, a color layer 410, an adhesive layer 435, and a carrier layer 415.

In some embodiments, the flexible substrate 400 includes an adhesive layer 415, disposed on top of the color layer 110. In some embodiments, the adhesive layer 415 is a primer. In some embodiments, the adhesive layer 415 is a skin adhesive. In some embodiments, the adhesive layer 415 is an acrylic or acetate adhesive. In some embodiments, the color layer 410 is formulated so that the color layer 410 adheres to the adhesive layer 415 but not the surface.

In operation, the carrier layer 415 is removed from the flexible substrate 400 and the flexible substrate 400 is applied to the surface. In this embodiment, there is no need to apply a primer to the surface before applying the flexible substrate 400. The adhesive layer 415 transfers to the surface and adheres to the color layer 410 so that the color layer 410 is adhered to the surface.

Figure 4B:
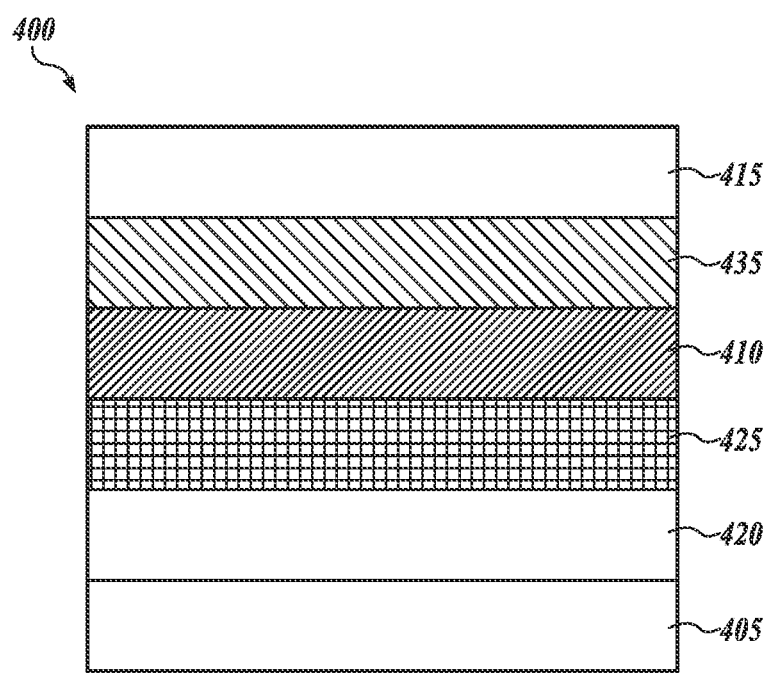
FIG. 4B is another example flexible substrate, in accordance with the present technology.

FIG. 4B is another example flexible substrate 400, in accordance with the present technology. In some embodiments, the flexible substrate 400 may include both an adhesive layer 435 and a pattern layer 425. In some embodiments, the adhesive layer 435 may adhere to both the color layer 410 and the pattern layer 425. In some embodiments, the adhesive layer 435 may be between the color layer 410 and the pattern layer 425. In some embodiments, the pattern layer 425 may be two-dimensional or three dimensional. In some embodiments, the pattern layer may be or include glitter, shimmer, rhinestones, stickers, appliques, etc. In some embodiments, the adhesive layer 435 is configured to specifically adhere to the pattern layer 425.

Figure 5A:
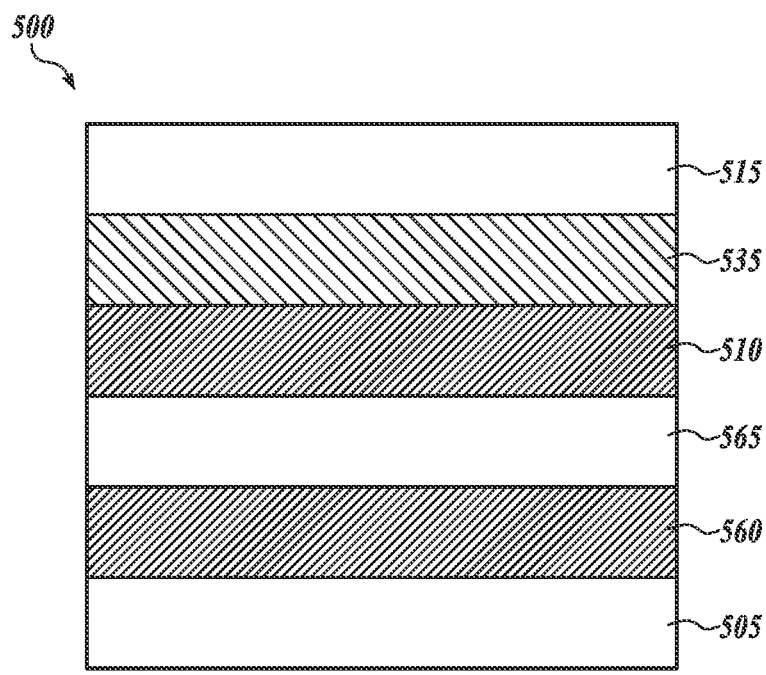
FIG. 5A is another example flexible substrate, in accordance with the present technology.

FIG. 5A is another example flexible substrate 500, in accordance with the present technology. In some embodiments, the flexible substrate 500 includes a transparent release 505, a first color layer 510, a second color layer 560, a lacquer layer 565, an adhesive layer 535, and a carrier layer 515.

In some embodiments, the flexible substrate 500 includes both a first color layer 510 and a second color layer 560. While only a first color layer 510 and a second color layer 560 are illustrated, the flexible substrate 500 may include any number of color layers. In some embodiments, the first color layer 510 and the second color layer 560 are configured to mix when applied. In some embodiments, the first color layer 510 and the second color layer 560 may be shaped or positioned distinctly, so that they are applied to different areas when pressure is applied to the flexible substrate 500. In some embodiments, the second color layer 560 is smaller than the first color layer 510, so that when pressure is applied to the flexible substrate 500, the second color layer 560 covers some, but not all of the first color layer 510. In some embodiments, the second color layer 560 is thinner than the first color layer 510 so that the second color layer 560 transfers a sheer or translucent color to the surface. In some embodiments, only a portion of the second color layer 560 is thinner only in certain areas of the second color layer 560, so that only a portion of the transferred second color is sheer or translucent. In this manner, in some embodiments, applying pressure to the flexible substrate 500 results in an ombre or gradient pattern of color when the first color layer 510 and the second color layer 560 interact. In some embodiments, the first color layer 510 and the second color layer 560 are multicolored.

In some embodiments, the flexible substrate 500 further includes a lacquer layer. In some embodiments, a lacquer layer 565 is provided between the first color layer 510 and the second color layer 560. In some embodiments, the lacquer layer 565 is configured to prevent the first color layer 510 and the second color layer 560 from mixing when transferred. In some embodiments, there is a lacquer layer 565 disposed below each color layer 510, 560. In some embodiments, the lacquer layer 565 provides a smooth, glossy finish to the surface. In some embodiments, the lacquer layer 565 is pigmented. In some embodiments, the lacquer layer 565 dries with a semi-matte finish. In some embodiments, the lacquer layer 560 includes a fragrance or a flavoring.

Figure 5B:
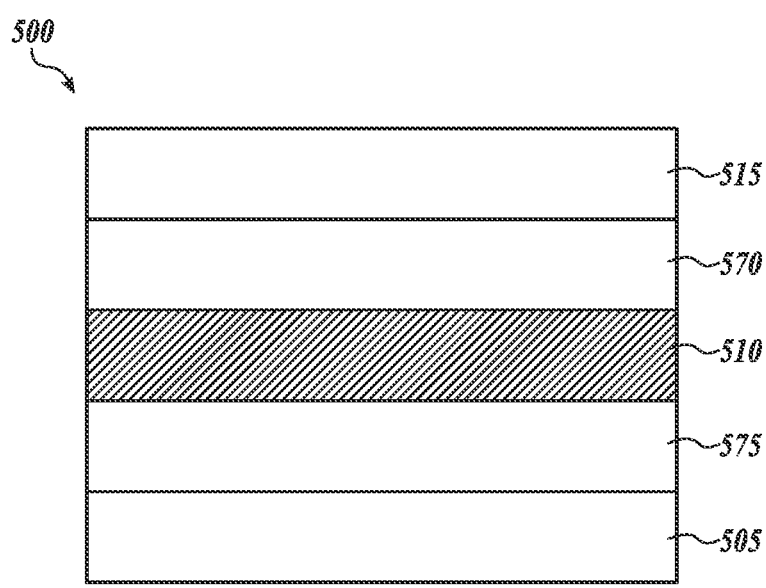
FIG. 5B is another example flexible substrate, in accordance with the present technology.

FIG. 5B is another example flexible substrate 500, in accordance with the present technology. In some embodiments, the flexible substrate 500 includes a transparent release 505, a finish layer 575, a color layer 510, an additive layer 570, and a carrier layer 515.

In some embodiments, the flexible substrate includes a finish layer 575. In some embodiments, the finish layer 575 is disposed below the color layer 510 on the flexible substrate 500. In some embodiments, the finish layer 575 is configured to provide a particular finish to the surface when transferred, such as glossy, matte, high-shine, frosted, satin, metallic, glitter, or sheer.

In some embodiments, the flexible substrate 500 includes one or more additive layers 570. In some embodiments, the additive layer 570 is selected from a UV protection layer, a moisturizing layer, a fragrance layer, a cooling layer, a heating layer, and an expanding layer. In some embodiments, the additive layer 570 is combined into the color layer 510, but in other embodiments, the additive layer 570 is separate from the color layer 510. In some embodiments, the additive layer 570 is disposed above the color layer 510 in the flexible substrate 500, such as when the additive layer 570 provides a benefit to the surface (for example, a moisturizing layer). In some embodiments, the additive layer 570 is disposed below the color layer 510 in the flexible substrate 500, such as when the additive layer 570 is a UV layer.

In some embodiments, the additive layer 570 is a cooling layer, a heating layer, or both. In some embodiments, the additive layer 570 includes menthol, methyl salicylate, capsaicin, or a combination thereof. In some embodiments, the additive layer 570 includes watermelon, yogurt, goji berries, aloe vera, mushroom, or a combination thereof. In some embodiments, the additive layer 570 includes peppermint oil, vanillyl butyl ether (AC-VBE), spearmint oil, camphor, *arnica*, or a combination thereof.

FIGS. 6A-6C illustrates an example method of using an example flexible substrate, in accordance with the present technology.

FIG. 6A shows an example flexible substrate 600, including a transparent release 605, a protective layer 620, a pattern layer 625, a color layer 610, and a carrier layer 615. In some embodiments, the color layer 610 includes an adhesive. In some embodiments, the flexible substrate 600 has a separate adhesive layer (such as shown in FIG. 5A).

The bottom image of FIG. 6A shows an example flexible substrate 600, where the carrier layer 615 is being removed. In some embodiments, the carrier layer 615 can be peeled from the flexible substrate 600 to expose the topmost layer of the flexible substrate 600 (illustrated here as the color layer 610).

FIG. 6B shows a user 1000 using the flexible substrate 600 on a surface (illustrated here as a top and bottom lip). In some embodiments, the surface is skin. In some embodiments, the surface is a top and bottom lip, but in other embodiments, the surface may be an eyelid, a cheek, only a top lip, only a bottom lip, an eyebrow, etc. In some embodiments, the user 1000 applies the flexible substrate 600 to the surface. The user 1000 may then apply pressure to the flexible substrate 600 by pressing on the transparent release (shown as 605 in FIG. 6A). In some embodiments, the color layer 610, the pattern layer 625, the protective layer 620, and any additional layer(s) of the flexible substrate described herein (except for the stencil layer 330) are transferred onto the surface only where the user 1000 applies pressure.

FIG. 6C shows a transfer 690 by the flexible substrate 600 onto the surface (illustrated as a top and bottom lip in FIG. 6C). In some embodiments, after pressing the flexible substrate 600 to the surface, one or more of the layers of the flexible substrate 600 is transferred onto the surface as the transfer 690.

FIGS. 7A-7D illustrates an example method of using a flexible substrate 700 and a primer 7000, in accordance with the present technology. In some embodiments, the method includes applying a primer 7000 before applying the flexible substrate 700.

Figure 7A:
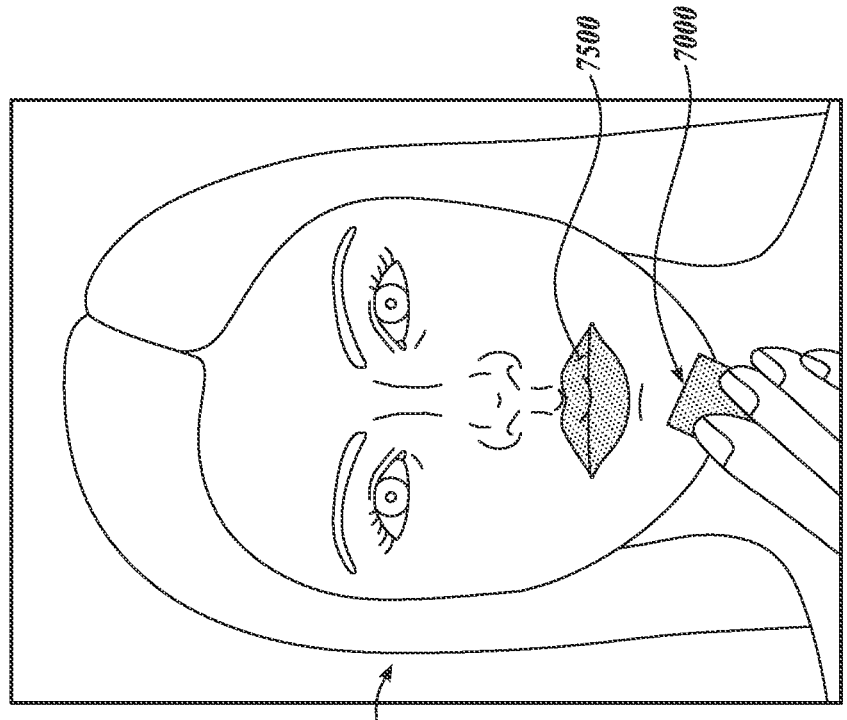
FIGS. 7A-7D illustrates an example method of using a flexible substrate and a primer, in accordance with the present technology.
Figure 7B:
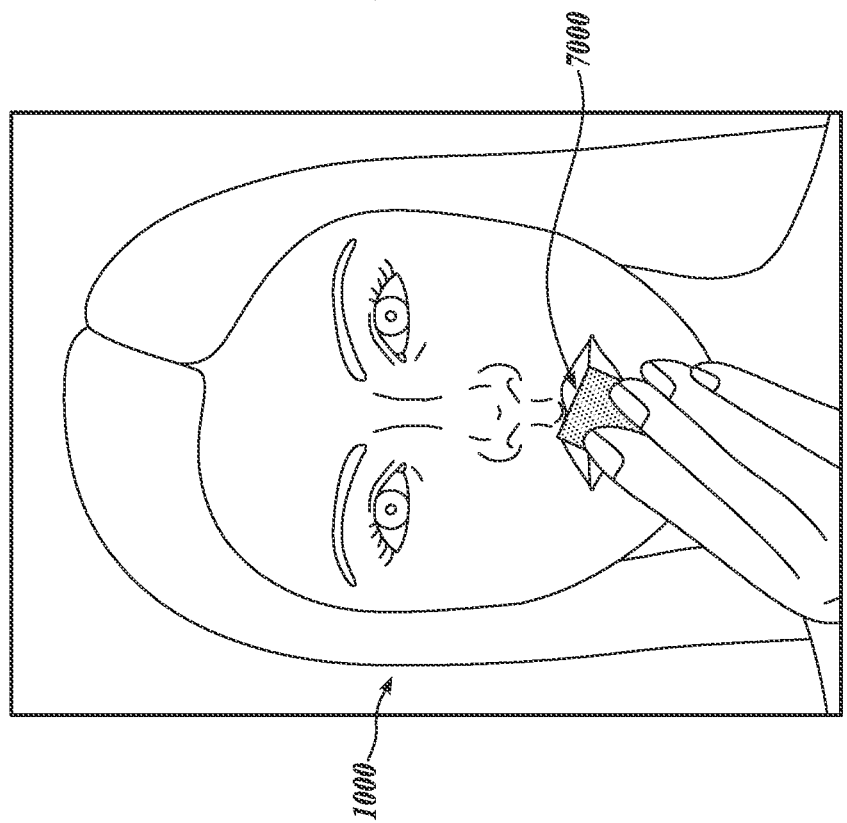

FIG. 7A shows a user 1000 applying the primer 7000. In some embodiments, the primer is an adhesive. In some embodiments, the primer is a high-solid emulsion adhesive. In some embodiments, the primer 7000 is a cream or liquid. In some embodiments, the primer 7000 is applied with a second flexible substrate, as illustrated in FIGS. 7A and 7B. In some embodiments, the primer 7000 is applied with an applicator, a wand, a compact, or a finger. In some embodiments, the primer 7000 is configured to adhere to a plurality of layers (such as a color layer and a pattern layer) of the flexible substrate 700, as described herein.

In FIG. 7B, the primer 7000 transferred onto a surface, illustrated here as a top and bottom lip of the user 1000. The primer 7000 creates a primed surface 7500. In some embodiments, the surface is skin. In some embodiments, the user may apply the primer 7000 to any portion or portions of the skin to create one or more primed surfaces 7500.

Figure 7C:
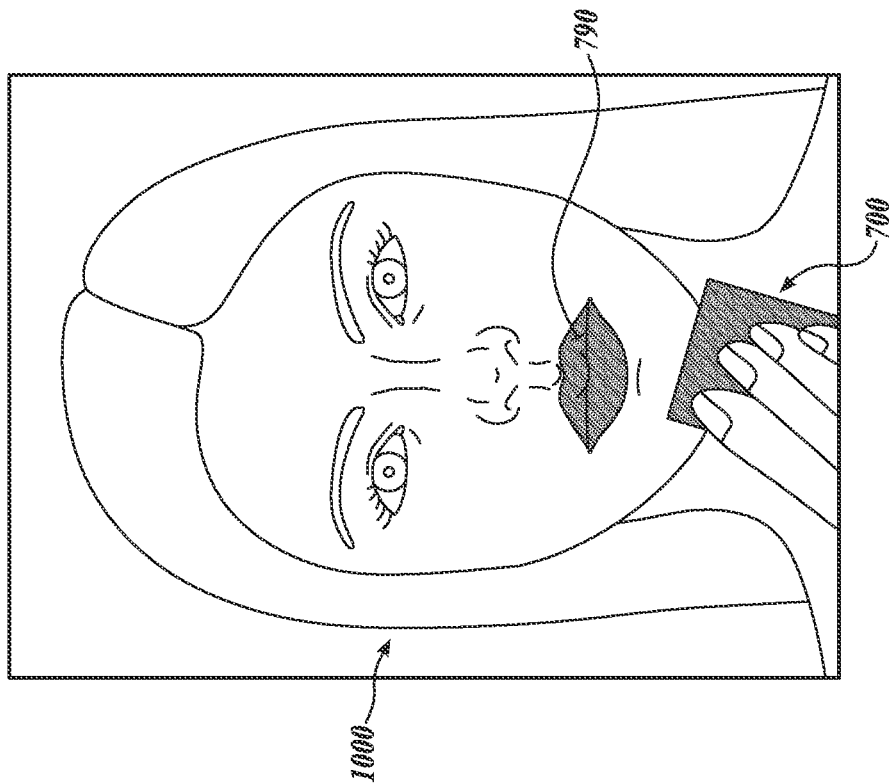

FIG. 7C shows a user 1000 using the flexible substrate 700 on a surface (illustrated here as a top and bottom lip). In some embodiments, the surface is skin. In some embodiments, the surface is a top and bottom lip, but in other embodiments, the surface may be an eyelid, a cheek, only a top lip, only a bottom lip, an eyebrow, etc. In some embodiments, the user 1000 applies the flexible substrate 700 to the surface. The user 1000 may then apply pressure to the flexible substrate 700 by pressing on the transparent release as described in FIG. 6B. In some embodiments, the color layer, the pattern layer, the protective layer, and any additional layer(s) of the flexible substrate described herein (except for the stencil layer) are transferred onto the surface only where the user 1000 applies pressure.

Figure 7D:
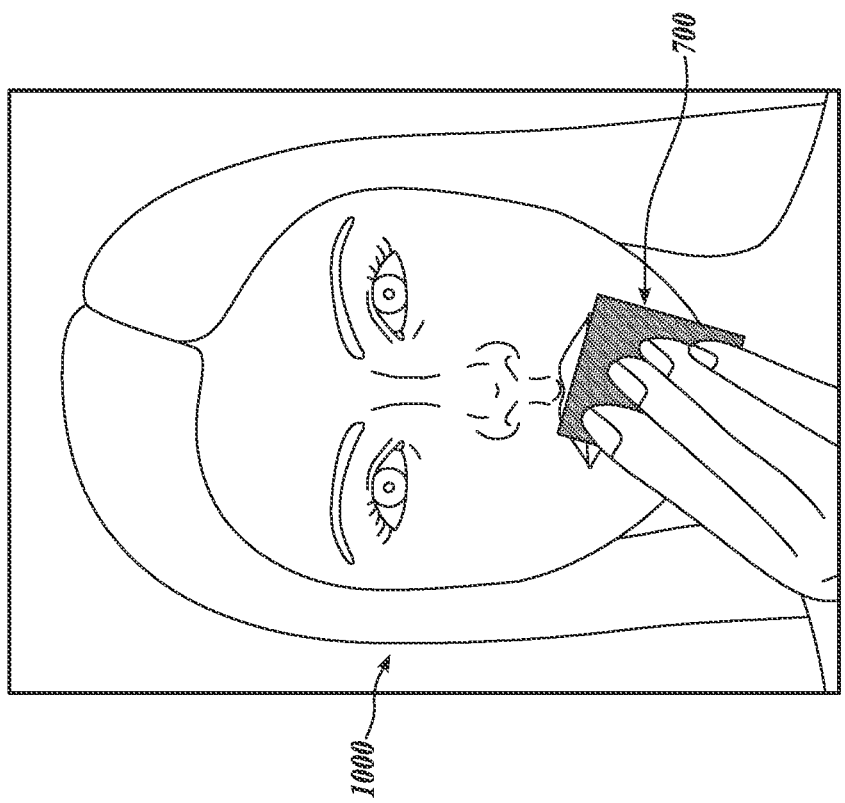

FIG. 7D shows a transfer 790 by the flexible substrate 700 onto the surface (illustrated as a top and bottom lip in FIG. 7D). In some embodiments, after pressing the flexible substrate 700 to the surface, one or more of the layers of the flexible substrate 700 is transferred onto the surface as the transfer 790.

In some embodiments, the plurality of layers of the flexible substrate 700 (such as a color layer, a pattern layer, and a protective layer, as described herein) are formulated to adhere to the primed surface 7500 and not the surface.

Figure 8:
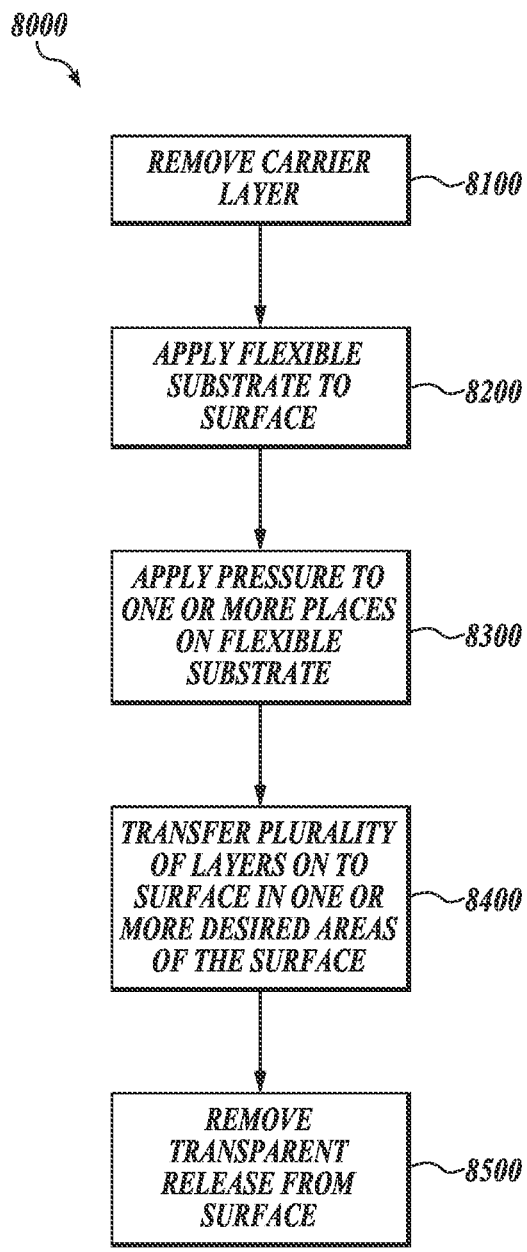
FIG. 8 illustrates an example method of applying a flexible substrate, in accordance with the present technology.

FIG. 8 illustrates an example method 8000 of applying a flexible substrate, in accordance with the present technology. Method 8000 begins in block 8100. In block 8100, the carrier layer is removed from the flexible substrate.

In block 8200, the flexible substrate is applied to a surface. In some embodiments, the surface is skin, but in other embodiments, the surface may be hair or nails. In some embodiments, the surface is a top and bottom lip, an eyelid, a cheek, a face, an eyebrow, etc.

In block 8300, pressure is applied to one or more places on the flexible substrate. A user, machine, or device may provide the pressure. The user, machine, or device presses on the transparent release with the plurality of layers (such as the color layer, the protective layer, the adhesive layer, or the additive layer as described herein) facing the surface.

In block 8400, the plurality of layers is transferred onto one or more desired areas of the surface. By pressing on only specific places on the flexible substrate, the user, machine, or device can transfer the layers to the one or more desired areas of the surface.

In block 8500, the transparent release is removed from the surface, and a transfer (such as transfer 690) is left on the surface. In some embodiments, the flexible substrate may be reusable. In this embodiment, the flexible substrate may be applied multiple times to produce a plurality of transfers.

Figure 9:
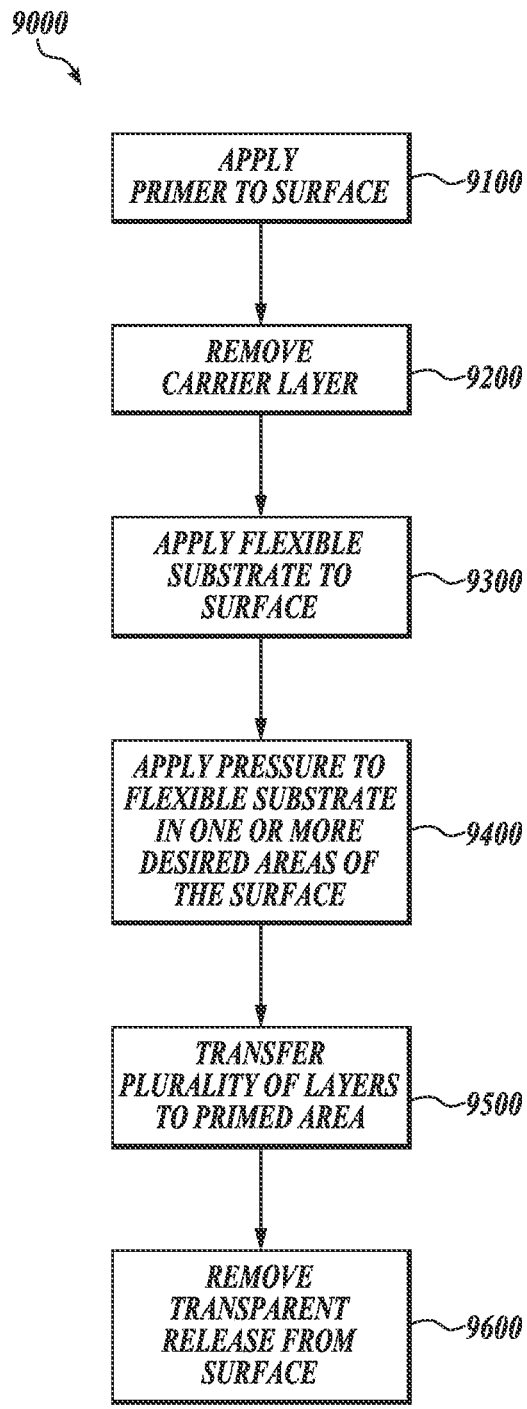
FIG. 9 illustrates another example method of applying a flexible substrate, in accordance with the present technology.

FIG. 9 illustrates another example method 9000 of applying a flexible substrate, in accordance with the present technology. The method 9000 begins in block 9100. In block 9100 a primer is applied to the surface. In some embodiments, the primer is applied with a second flexible substrate, as described in FIGS. 7A-7B. In some embodiments, the primer is applied to create one or more transfer areas, as shown in FIG. 7B.

In block 9200, the carrier layer of the flexible substrate is removed.

In block 9300, the flexible substrate is applied to a surface. In some embodiments, the surface is skin, but in other embodiments, the surface may be hair or nails. In some embodiments, the surface is a top and bottom lip, an eyelid, a cheek, a face, an eyebrow, etc.

In block 9400, pressure is applied to one or more places on the flexible substrate. A user, machine, or device may provide the pressure. The user, machine, or device presses on the transparent release (or release) with the plurality of layers (such as the color layer, the protective layer, the adhesive layer, or the additive layer as described herein) facing the surface.

In block 9500, the plurality of layers is transferred onto one or more desired areas of the surface. By pressing on only specific places on the flexible substrate, the user, machine, or device can transfer the layers to the one or more desired areas of the surface. In some embodiments, the plurality of layers is formulated so that they adhere to the one or more transfer areas, and not the surface that has not been coated in primer.

In block 9600, the transparent release (or release) is removed from the surface, and a transfer (such as transfer 690) is left on the surface. In some embodiments, the flexible substrate may be reusable. In this embodiment, the flexible substrate may be applied multiple times to produce a plurality of transfers.

Figure 10:
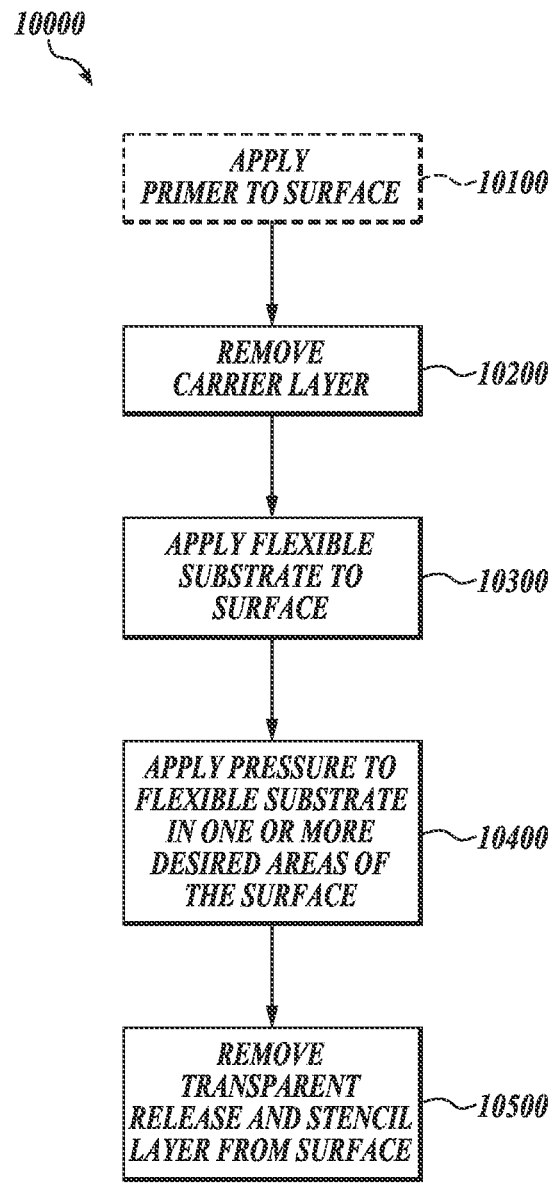
FIG. 10 illustrates another example method of applying a flexible substrate, in accordance with the present technology.

FIG. 10 illustrates another example method 10000 of applying a flexible substrate, in accordance with the present technology. Method 10000 may begin in block 10100. In some embodiments, block 10100 is optional. In block 10100 a primer is applied to the surface. In some embodiments, the primer is applied with a second flexible substrate, as described in FIGS. 7A-7B. In some embodiments, the primer is applied to create one or more transfer areas, as shown in FIG. 7B.

In block 10200, the carrier layer of the flexible substrate is removed.

In block 10300, pressure is applied to one or more places on the flexible substrate. A user, machine, or device may provide the pressure. The user, machine, or device presses on the transparent release (or release) with the plurality of layers (such as the color layer, the protective layer, the adhesive layer, or the additive layer as described herein) facing the surface.

In block 10400, the plurality of layers is transferred onto one or more desired areas of the surface. By pressing on only specific places on the flexible substrate, the user, machine, or device can transfer the layers to the one or more desired areas of the surface. In some embodiments, the plurality of layers are formulated so that they adhere to the one or more transfer areas, and not the surface that has not been coated in primer.

In block 10500, the transparent release (or release) is removed from the surface, and a transfer (such as transfer 690) is left on the surface. In some embodiments, the flexible substrate may be reusable. In this embodiment, the flexible substrate may be applied multiple times to produce a plurality of transfers.

The order in which some or all of the process blocks in methods 8000, 9000, and 10000 should not be deemed to be limiting. Rather, one or ordinary skill in the art having the benefit of the present disclosure will understand that some of the process blocks may be executed in a variety of orders not illustrated, or even in parallel.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate other embodiments within the scope of this disclosure may include structures and functionalities from more than one specific embodiment shown in the figures and described in the specification.

In the foregoing description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "vertical," "horizontal," "front," "rear," "left," "right," "top," and "bottom," etc. These references, and other similar references in the present application, are intended to assist in helping describe and understand the particular embodiment (such as when the embodiment is positioned for use) and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value. The term "based upon" means "based at least partially upon."

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The embodiments of the invention in which an exclusive property or privilege is claimed are defined as follows:

1. A flexible substrate comprising:
   a transparent release selected from polyethylene (PE), polyurethane (PU), biaxially-oriented polypropylene (BOPP), polyethylene terephthalate (PET), or combinations thereof;
   a protective layer disposed on top of the transparent release, wherein the protective layer is selected from a wax, a powder, or an oil;
   a cosmetic layer comprising a cosmetic and a fragrance disposed on top of the protective layer, wherein the cosmetic is selected from a lip color, a lip tint, an eyeshadow, a blush, or an eyeliner; and
   a silicon release layer removably disposed on top of the cosmetic layer, wherein the silicon release layer is configured to prevent the cosmetic layer from transferring.

2. The flexible substrate of claim 1, wherein the flexible substrate further comprises a pattern layer including a binder and a pigment.

3. The flexible substrate of claim 1, wherein the flexible substrate further comprises a stencil layer comprising one or more openings.

4. The flexible substrate of claim 1, wherein the flexible substrate further comprises one or more additive layers comprised of one or more additive.

5. The flexible substrate of claim 4, wherein the one or more additives are selected from: a UV protection additive; a moisturizer; a cooling additive; and a heating additive.

6. The flexible substrate of claim 1, wherein the flexible substrate further comprises an adhesive layer, wherein the adhesive layer is disposed on top of the cosmetic layer.

7. The flexible substrate of claim 1, wherein the flexible substrate further comprises a finish layer comprising a glitter, shimmer, shine, matte, frosted, satin, metallic, or sheer cosmetic.

8. A system comprising:
   the flexible substrate of claim 1; and
   a primer.

9. The system of claim 8, wherein the primer is a high-solid emulsion adhesive.

10. The system of claim 8, wherein the flexible substrate further comprises a pattern layer disposed underneath the cosmetic layer.

11. The system of claim 8, wherein the flexible substrate further comprises a stencil layer comprising one or more openings, wherein the stencil layer is on top of the cosmetic layer.

12. The system of claim 8, wherein the flexible substrate further comprises one or more additive layers comprised of one or more additives.

13. The system of claim 12, wherein the one or more additives are selected from a UV protection; a moisturizer; a cooling additive; and a heating additive.

14. A method of applying a cosmetic with the flexible substrate of claim 1, the method comprising:
    removing the silicon release layer from the flexible substrate of claim 1;
    applying the flexible substrate to a surface;
    applying pressure to the flexible substrate in one or more places corresponding with one or more desired locations of the surface;
    transferring the cosmetic layer and the protective layer to the surface; and
    removing the transparent release from the surface.

15. The method of claim 14, wherein the method further comprises:
    applying a primer to the one or more desired locations of the surface before applying the flexible substrate, wherein the primer is configured to adhere to the cosmetic layer and the protective layer.

16. The method of claim 14, wherein the method further comprises:
    applying the flexible substrate to the surface, wherein the flexible substrate further comprises a stencil layer comprising a plurality of openings;
    applying pressure to the flexible substrate in one or more places corresponding with one or more desired locations of the surface;
    transferring the cosmetic layer and the protective layer through the one or more openings; and
    removing the stencil layer from the surface.

17. The method of claim 14, wherein the method further comprises:
    applying a stencil layer to the surface before applying the flexible substrate to the surface, wherein the stencil layer comprises a plurality of openings;
    applying pressure to the flexible substrate in one or more places corresponding with one or more desired locations of the surface;
    transferring the cosmetic layer and the protective layer through the one or more openings; and
    removing the stencil layer from the surface.

18. The method of claim 14, wherein the method further comprises transferring a pattern layer of the flexible substrate to the surface.

19. The method of claim 14, wherein the method further comprises transferring one or more additive layers of the flexible substrate to the surface.

20. The flexible substrate of claim 1, wherein the protective layer is selected from beeswax, candelilla wax, polyolefin wax, setting powder, translucent powder, talcum powder, mineral oil, castor oil, lanolin oil, silicon oil, vegetable oil, or a combination thereof.

* * * * *